(12) United States Patent
Laiho et al.

(10) Patent No.: US 9,574,116 B2
(45) Date of Patent: Feb. 21, 2017

(54) ADHESIVE PROPYLENE POLYMER COMPOSITION SUITABLE FOR EXTRUSION COATING OF PAPER SUBSTRATES

(71) Applicant: Borealis AG, Vienna (AT)

(72) Inventors: Erkki Laiho, Helsinki (FI); Auli Nummila-Pakarinen, Porvoo (FI); Elke Pachner, Wels (AT); Hanna Rajala, Tampere (FI); Markku Sainio, Porvoo (FI); Juha Yli-Peltola, Helsinki (FI)

(73) Assignee: Borealis, AG, Vienna (AT)

( * ) Notice: Subject to any disclaimer, the term of this patent is extended or adjusted under 35 U.S.C. 154(b) by 175 days.

(21) Appl. No.: 14/534,701

(22) Filed: Nov. 6, 2014

(65) Prior Publication Data

US 2015/0064487 A1    Mar. 5, 2015

Related U.S. Application Data

(63) Continuation of application No. 12/990,026, filed as application No. PCT/EP2009/054892 on Apr. 23, 2009, now abandoned.

(30) Foreign Application Priority Data

Apr. 28, 2008  (EP) .................... 08103741

(51) Int. Cl.
| | | |
|---|---|---|
| C09J 123/00 | (2006.01) | |
| C09J 123/12 | (2006.01) | |
| B32B 27/10 | (2006.01) | |
| C09J 123/10 | (2006.01) | |
| C09J 5/00 | (2006.01) | |
| C09J 123/30 | (2006.01) | |
| B32B 25/06 | (2006.01) | |
| B32B 27/14 | (2006.01) | |
| B32B 27/18 | (2006.01) | |
| B32B 27/20 | (2006.01) | |
| B32B 27/30 | (2006.01) | |
| B32B 27/32 | (2006.01) | |
| C08L 23/08 | (2006.01) | |
| C08L 51/06 | (2006.01) | |

(52) U.S. Cl.
CPC .............. *C09J 123/12* (2013.01); *A61B 50/30* (2016.02); *B32B 25/06* (2013.01); *B32B 27/10* (2013.01); *B32B 27/14* (2013.01); *B32B 27/18* (2013.01); *B32B 27/20* (2013.01); *B32B 27/306* (2013.01); *B32B 27/32* (2013.01); *B32B 27/327* (2013.01); *C09J 5/00* (2013.01); *C09J 123/10* (2013.01); *C09J 123/30* (2013.01); *A61B 50/33* (2016.02); *A61B 2050/3008* (2016.02); *B32B 2255/12* (2013.01); *B32B 2270/00* (2013.01); *B32B 2307/30* (2013.01); *B32B 2307/306* (2013.01); *B32B 2307/412* (2013.01); *B32B 2307/50* (2013.01); *B32B 2323/10* (2013.01); *B32B 2439/70* (2013.01); *B32B 2439/80* (2013.01); *B32B 2553/00* (2013.01); *C08L 23/0853* (2013.01); *C08L 51/06* (2013.01); *C09J 2423/10* (2013.01); *Y10T 428/31808* (2015.04); *Y10T 428/31895* (2015.04); *Y10T 428/31899* (2015.04); *Y10T 428/31902* (2015.04); *Y10T 428/31906* (2015.04)

(58) Field of Classification Search
CPC .......... C09J 123/12; C09J 5/00; C09J 123/10; C09J 123/30; C09J 2423/10; A61B 50/30; A61B 2050/3008; A61B 50/33; B32B 25/06; B32B 27/10; B32B 27/14; B32B 27/18; B32B 27/20; B32B 27/308; B32B 27/32; B27B 27/327; Y10T 428/31808; Y10T 428/31895; Y10T 428/31899; Y10T 428/31902

See application file for complete search history.

(56) References Cited

U.S. PATENT DOCUMENTS

| 5,998,547 A | 12/1999 | Hohner |
| 6,433,109 B1 | 8/2002 | Raetzsch et al. |
| 6,992,146 B2 | 1/2006 | McLoughlin et al. |
| 2001/0038938 A1 | 11/2001 | Takahashi et al. |
| 2002/0127389 A1 | 9/2002 | Hanada et al. |
| 2004/0127614 A1 | 7/2004 | Jiang et al. |

FOREIGN PATENT DOCUMENTS

| CN | 101092500 A | 12/2007 |
| EP | 571882 A2 | 12/1993 |

(Continued)

OTHER PUBLICATIONS

International Search Report for PCT/EP2009/054892, mailed Aug. 25, 2009.

(Continued)

*Primary Examiner* — Nathan M Nutter
(74) *Attorney, Agent, or Firm* — Milbank, Tweed, Hadley McCloy LLP

(57) ABSTRACT

Two-component adhesion composition suitable for extrusion coating paper substrates which comprises:
a) from 70 to 98 wt % of high melt strength polypropylene (A) with a branching index g' of 0.9 or less; and
b) from 2 to 30 wt % of a component (B) selected from the group consisting of:
(i) maleic anhydride-modified polypropylene (MAPP);
(ii) maleic anhydride-modified polypropylene wax;
(iii) polypropylene homopolymer with high melt flow rate; or
(iv) ethylene-vinyl acetate-based hot melt adhesive, and its use.

8 Claims, No Drawings

(56) References Cited

FOREIGN PATENT DOCUMENTS

| | | |
|---|---|---|
| EP | 1 479 716 A1 | 11/2004 |
| EP | 1609890 A1 | 12/2005 |
| WO | 99/50350 A1 | 10/1999 |
| WO | 00/00520 A1 | 1/2000 |
| WO | 00/56794 A1 | 9/2000 |
| WO | 00/69982 A1 | 11/2000 |
| WO | 2004018528 A1 | 3/2004 |
| WO | 2004046214 A2 | 6/2004 |
| WO | 2006/043815 A1 | 4/2006 |

OTHER PUBLICATIONS

International Preliminary Examination Report for PCT/EP2009/054892, mailed Jul. 8, 2010.

ADHESIVE PROPYLENE POLYMER COMPOSITION SUITABLE FOR EXTRUSION COATING OF PAPER SUBSTRATES

This application is a continuation application of U.S. application Ser. No. 12/990,026, filed on Jan. 10, 2011, as National Stage Application under 35 U.S.C. §371 of PCT/EP2009/054892, filed Apr. 23, 2009, which claims priority to European Application No. EP 08103741.8, filed Apr. 28, 2008, the disclosures of which are incorporated by reference here in their entireties.

The present invention relates to polypropylene-based adhesive compositions, which are suitable for extrusion coating especially of paper substrates.

In general, extrusion coating of substrates such as paper, paperboard, fabrics and metal foils with a thin layer of plastic is practiced on a large scale. The polymer is extruded first whereby the flux of molten polymeric material passes through a fat die to obtain a film a few microns thick, followed by a coating step, whereby the film is laid on a support and passes on a cooling cylinder. Upon cooling, the polymer adheres to its support.

Low density polyethylene (LDPE) is mainly used in extrusion coating because of the ease in processing although stiffness, barrier properties and temperature resistance of LDPE are often not satisfactory.

Polypropylene, also known as propylene polymer, is a well-known commercial polymer, which is used for a variety of products, such as packaging films and moulded shapes.

Commercial propylene polymers exhibit several desirable properties, such as good heat tolerance and transparency, which make polypropylene polymers interesting in many application fields.

However, since many polypropylene materials suffer from low melt strength and low melt extensibility, they show poor processability in high speed extrusion coating. Further, the adhesion of polypropylene on substrates like paper is not satisfactory. For these reasons only a few polypropylene-based systems are available in the industry for extrusion coating at present.

Many efforts have been undertaken to improve the processing properties of polypropylene polymers. The shortcomings during processing have partially been overcome by the class of high melt strength polypropylene. Such polymers are featured by the introduction of branchings in the linear polymer backbone. This can be achieved through post-reactor treatment, copolymerization with dienes, and through polymerization with specific catalysts at high temperatures.

Although these branched polymer types have improved properties, there is still the desire to improve their adhesion to substrates such as paper.

To improve the adhesion between the substrate and the plastic layer different methods are commonly known, such as ozone treatment of the molten polymer film, flame treatment and corona treatment of the substrate or the use of an adhesive layer.

Various further proposals have been made to increase the adhesion of propylene polymer layers to different substrates.

For example, U.S. Pat. No. 4,394,485 discloses four component adhesive blends comprising modified polyolefin resins with improved adhesion to polar substrates such as metal, glass, paper, etc. The blend consists of high density polyethylene (HDPE), LDPE, a polypropylene homo- or copolymer and a polyethylene polymer grafted with carboxylic acid or acid derivate and can be used in processes like lamination, coextrusion, powder and/or extrusion coating, blow molding, etc. The presence of polyethylene components will necessarily limit the thermal stability of these compositions.

According to U.S. Pat. No. 4,394,485 adhesion tests have been done by heat sealing of compression molded films into substrates, which is not comparable to the extrusion coating process due the residence time, temperature and thickness of the coating. Nevertheless, an improved adhesion to rather unporous substrates like polypropylene (PP) and ethylene-vinyl alcohol (EVOH) films, and aluminum foil was observed.

WO 00/69982 describes adhesive propylene polymer compositions suitable for coating substrates, which show improved adhesion to metals without the need for a primer coating or to polymeric substrates, with a primer coating without the need for post heating.

This blend consists of three components comprising (a) 50 to 80 wt % of an unmodified propylene polymer, which may be a homo- or a copolymer, a heterophasic propylene polymer or mixtures thereof, (b) 10 to 30 wt % of a high melt strength propylene polymer and (c) 3 to 30 wt % of a modified propylene polymer grafted with an unsaturated compound having a polar group, wherein the total of (a), (b) and (c) is 100%.

U.S. Pat. No. 4,957,968 describes a three component adhesive thermoplastic elastomer blend, which is adherent to metal, glass, wood, polyolefins and polar polymers with no pretreatment or use of other adhesives.

The three components are (a) a polyolefin modified by a chemically reactive functional group, (b) a polymer prepared from one or more of the following: ethylene, propylene, butylene, isobutylene, octene-1,4-methyl-pentene-1, hexene-1 and (c) an olefinic elastomer. For example such a blend comprises (a) maleic anhydride modified polypropylene, (b) polypropylene and (c) ethylene propylene diene rubber.

WO 00/31181 describes wettable polypropylene compositions comprising up to 85 wt % of unmodified polypropylene and up to 35 wt % of a hydrophilic, polar compound which includes functional sites selected from the group consisting of carboxyl, hydroxyl, ether or ester moieties. For example maleic anhydride-modified polypropylene (MAPP) can be used as polar compound. To provide permanent wettability a mixture from unmodified polypropylene with e.g. MAPP is treated with hot potassium hydroxide. The composition can be used for example to achieve a wettable polypropylene extrusion coating on paper or paperboard for use in packaging applications where stiffness and printability is important.

Although much development work has been done in the field of adhesive propylene polymer compositions, there is a continuous need for alternative or improved adhesive propylene polymer compositions, which can be used in extrusion coating for paper substrates and which show an improved adhesion to the substrate compared to known propylene polymer materials, high melt strength propylene polymers and blends thereof.

OBJECT OF THE INVENTION

An object of the invention is therefore to provide polypropylene compositions, which are particularly suitable for extrusion coating on paper substrates, having high melt strength and improved adhesion to paper or paperboard without the need of surface treating methods or additional adhesion layers.

A further object of the invention is the use of the polypropylene composition in extrusion coating processes using paper or paperboard as substrate.

Another object of the present invention is to provide a substrate or article which has at least one layer of highly adherent propylene polymer composition on at least one surface.

SUMMARY OF THE INVENTION

The present invention relates to polypropylene compositions useable for extrusion coating of paper substrates and showing improved adhesion to the substrate, yielding extrusion coating products of high quality.

Particularly, the present invention deals with two component adhesion compositions suitable for extrusion coating paper substrates comprising a blend of high melt strength polypropylene and one component selected from the group of
  (i) maleic anhydride-modified polypropylene (MAPP)
  (ii) maleic anhydride-modified polypropylene wax
  (iii) polypropylene homopolymer with high melt flow rate
     or
  (iv) ethylene-vinyl acetate-based hot melt adhesive

DETAILED DESCRIPTION OF THE INVENTION

It has now been discovered that the problems and deficiencies relating to the compositions and blends according to the state of the art regarding insufficient adhesion to paper or paperboard substrates can be avoided or at least significantly decreased with a composition according to the present invention. It has been noted that certain combinations of high melt strength polypropylene with special polypropylenes or an ethylene-vinyl acetate-based hot melt adhesive meet the objectives.

The two component adhesion composition suitable for extrusion coating paper substrates according to the invention comprises:
  a) from 70 to 98 wt %, preferably 75 to 95 wt % of high melt strength polypropylene (A) with a branching index g' of 0.9 or less and
  b) from 2 to 30 wt %, preferably 5 to 25 wt % of a component (B) selected from the group of
    (i) maleic anhydride-modified polypropylene (MAPP)
    (ii) maleic anhydride-modified polypropylene wax
    (iii) polypropylene homopolymer with high melt flow rate
       or
    (iv) ethylene-vinyl acetate-based hot melt adhesive Thus the first mandatory component in the present invention is a polypropylene (A) characterized by a certain degree of branching. Possible polypropylenes (A) are so called Y/H-polypropylenes and are for instance described in EP 0 787 750, i.e. single branched polypropylene types (Y polypropylenes having a backbone with a single long side-chain and an architecture resembles a "Y") and polypropylene types in which polymer chains are coupled with a bridging group (an architecture resembles a "H"), as well as multi-branched polypropylenes, i.e. not only the polypropylene backbone is furnished with a larger number of side chains (branched polypropylene) but also some of the side chains themselves. Such polypropylenes are characterized by rather high melt strength.

A parameter of the degree of branching is the branching index g'. The branching index g' correlates with the amount of branches of a polymer. The branching index g' is defined as $g'=[IV]_{br}/[IV]_{lin}$ which g' is the branching index, $[IV]_{br}]$ is the intrinsic viscosity of the branched polypropylene and $[IV]_{lin}$ is the intrinsic viscosity of the linear polypropylene having the same weight average molecular weight (within a range of ±10%) as the branched polypropylene. Thereby, a low g'-value is an indicator for a high branched polymer. In other words, if the g'-value decreases, the branching of the polypropylene increases. Reference is made in this context to B. H. Zimm and W. H. Stockmeyer, J. Chem. Phys. 17, 1301 (1949). This document is herewith included by reference.

The intrinsic viscosity needed for determining the branching index g' is measured according to DIN ISO 1628/1 October 1999 (in Decalin at 135° C.).

Thus it is preferred that the branching index g' of the polypropylene (A) shall be less than 0.9, more preferably equal or less than 0.8. In another preferred embodiment the branching index g' of the polypropylene (A) shall be preferably less than 0.7.

The polypropylene (A) can be a propylene homopolymer or a propylene copolymer, wherein the homopolymer is preferred.

Accordingly, the homopolymer as well as the copolymer can be a unimodal or multimodal polymer composition.

In a preferred embodiment the polypropylene is preferably unimodal. In another preferred embodiment the polypropylene is preferably multimodal, more preferably bimodal.

"Multimodal" or "multimodal distribution" describes a frequency distribution that has several relative maxima. In particular, the expression "modality of a polymer" refers to the form of its molecular weight distribution (MWD) curve, i.e. the appearance of the graph of the polymer weight fraction as a function of its molecular weight. If the polymer is produced in the sequential step process, i.e. by utilizing reactors coupled in series, and using different conditions in each reactor, the different polymer fractions produced in the different reactors each have their own molecular weight distribution which may considerably differ from one another. The molecular weight distribution curve of the resulting final polymer can be seen at a super-imposing of the molecular weight distribution curves of the polymer fraction which will, accordingly, show a more distinct maxima, or at least be distinctively broadened compared with the curves for individual fractions.

A polymer showing such molecular weight distribution curve is called bimodal or multimodal, respectively.

The expression homopolymer used in the instant invention relates to a polypropylene that consists substantially, i.e. of at least 97 wt %, preferably of at least 99 wt %, and most preferably of at least 99.8 wt % of propylene units. In a preferred embodiment only propylene units in the propylene homopolymer are detectable. The comonomer content can be determined with FT infrared spectroscopy, as described below in the examples.

In case the polypropylene according to this invention is a propylene copolymer, it is preferred that the comonomer is ethylene. However, also other comonomers known in the art are suitable. Preferably, the total amount of comonomer, more preferably ethylene, in the propylene copolymer is up to 15 wt %, more preferably up to 10 wt %.

It is also possible that the polypropylene is a propylene copolymer comprising a polypropylene matrix and an ethylene-propylene rubber (EPR).

The polypropylene matrix can be a homopolymer or a copolymer, more preferably multimodal, i.e. bimodal, homopolymer or a multimodal, i.e. bimodal, copolymer. In case the polypropylene matrix is a propylene copolymer, then it is preferred that the comonomer is ethylene or butene. However, also other comonomers known in the art are suitable. The preferred amount of comonomer, more preferably ethylene, in the polypropylene matrix is up to 8.00 mol %. In case the propylene copolymer matrix has ethylene as the comonomer component, it is in particular preferred that the amount of ethylene in the matrix is up to 8.00 mol %, more preferably less than 6.00 mol %. In case the propylene copolymer matrix has butene as the comonomer component, it is in particular preferred that the amount of butene in the matrix is up to 6.00 mol % more preferably less than 4.00 mol %.

Preferably, the ethylene-propylene rubber (EPR) in the total propylene copolymer is up to 60 wt %. More preferably the amount of ethylene-propylene rubber (EPR) in the total propylene copolymer is in the range of 15 to 60 wt % still more preferably in the range of 20 to 50 wt %.

In addition, it is preferred that the polypropylene being a copolymer comprising a polypropylene matrix and an ethylene-propylene rubber (EPR) has an ethylene-propylene rubber (EPR) with an ethylene-content of up to 65 wt %.

The high degree of branching of the polypropylene (A) contributes also to its melt strength. Accordingly it is preferred that the polypropylene (A) is further characterized by a melt strength of at least 10 cN at a maximum speed of at least 200 mm/s, more preferably by a melt strength of at least 20 cN at a maximum speed of at least 200 mm/s, still more preferably by a melt strength of at least 25 cN at a maximum speed of at least 200 mm/s, yet more preferably by a melt strength of at least 25 cN at a maximum speed of at least 250 mm/s. The measuring of the melt strength has been undertaken by a temperature of 200° C. with an acceleration of the melt strand drawn down of 120 mm/sec$^2$. The exact measuring method is defined in the example section.

Furthermore, it is preferred that the polypropylene has a melt flow rate (MFR) given in a specific range. The melt flow rate mainly depends on the average molecular weight. This is due to the fact that long molecules render the material a lower flow tendency than short molecules. An increase in molecular weight means a decrease in the MFR-value. The melt flow rate (MFR) is measured in g/10 min of the polymer discharged through a defined die under specified temperature and pressure conditions and the measure of viscosity of the polymer which, in turn, for each type of polymer is mainly influenced by its molecular weight but also by its degree of branching. The melt flow rate measured under a load of 2.16 kg at 230° C. (ISO 1133) is denoted as MFR$_2$ (230° C.). Accordingly, it is preferred that in the present invention the polypropylene (A) has an MFR$_2$ (230° C.) in a range of 0.01 to 100 g/10 min, more preferably of 0.10 to 50 g/10 min, still more preferred of 1.00 to 25 g/10 min.

Preferably the cross-linked fraction of the polypropylene (A) does not exceed 1.0 wt.-%, even more preferred does not exceed 0.8 wt.-%, still more preferred does not exceed 0.5 wt.-% determined as the relative amount of polymer insoluble in boiling xylene (xylene hot insoluble fraction, XHI).

More preferably, the polypropylene of the instant invention is isotactic. Thus the polypropylene according to this invention shall have a rather high pentade concentration, i.e. higher than 90%, more preferably higher than 92% and most preferably higher than 93%. In another preferred embodiment the pentade concentration is higher than 95%. The pentade concentration is an indicator for the narrowness in the stereoregularity distribution of the polypropylene.

The high melt strength polypropylene (A) can be preferably further defined by the way obtained.

Accordingly the polypropylene (A) can be the result of treating an unmodified polypropylene (A') with thermally decomposing radical-forming agents and/or with ionizing radiation, where both treatments may optionally be accompanied or followed by a treatment with bi- or multifunctionally unsaturated monomers, e.g. butadiene, isoprene, dimethylbutadiene or divinylbenzene. A suitable method to obtain the polypropylene (A) is for instance disclosed in EP 0 879 830 A1 and EP 0 890 612 A2. Both documents are herewith included by reference.

The unmodified polypropylene (A') has preferably a MFR$_2$ (230° C.) in a range of 0.05 to 45.00 g/10 min. More preferably the MFR$_2$ (230° C.) is in a range of 0.05 to 35.00 g/10 min in case the unmodified polypropylene (A') is a homopolymer. On the other hand the MFR$_2$ (230° C.) is in a range of 0.05 to 45.00 g/10 min in case the unmodified polypropylene (A') is a copolymer.

Preferably the unmodified polypropylene (A') comprises 85.0 to 99.9 wt.-% of propylene and 0.1 to 15.0 wt % of one or more α-olefins with 2 or 4 to 18 carbon atoms, in particular ethylene.

As stated above the unmodified polypropylene (A') is preferably multimodal, more preferably bimodal. Accordingly it is preferred that the unmodified polypropylene (A') has a molecular weight distribution (MWD) of 5 to 60, more preferably in the range of 15 to 35.

Moreover the unmodified polypropylene (A') has preferably a weight average molecular weight (Mw) of 500,000 to 1,500,000 g/mol, more preferably in the range of 600,000 to 1,000,000 g/mole. The number average molecular weight (M$_n$) preferably ranges of 25,000 to 100,000 g/mol and more preferably of 30,000 to 100,000 g/mol.

The number average molecular weight (Mn) and the weight average molecular weight (Mw) as well as the molecular weight distribution (MWD) are determined in the instant invention by size exclusion chromatography (SEC) using Waters Alliance GPCV 2000 instrument with online viscometer. The oven temperature is 140° C. Trichlorobenzene is used as a solvent (ISO 16014).

The peroxide used for the manufacture of polypropylene (A) is preferably a thermally decomposing free radical-forming agent, more preferably selected from the group consisting of acyl peroxide, alkyl peroxide, hydroperoxide, perester and peroxycarbonate.

The following listed peroxides are in particular preferred:
  Acyl peroxides: benzoyl peroxide, 4-chlorobenzoyl peroxide, 3-methoxybenzoyl peroxide and/or methyl benzoyl peroxide.
  Alkyl peroxides: altyl t-butyl peroxide, 2,2-bis(t-butylperoxybutane), 1,1-bis(t-butylperoxy)-3,3,5-trimethylcyclohexane, n-butyl-4-4-bis(t-butylperoxy) valerate, diisopropylaminomethyl-t-amyl peroxide, dimethylaminomethyl-t-amyl peroxide, diethylaminomethyl-t-butyl peroxide, dimethylaminomethyl-t-butyl peroxide, 1,1-di-(t-amylperoxy)cyclohexane, t-amyl peroxide, t-butylcumyl peroxide, t-butyl peroxide and/or 1-hydroxybutyl n-butyl peroxide.
  Peresters and peroxy carbonates: butyl peracetate, cumyl peracetate, cumyl perpropionate, cyclohexyl peracetate, di-t-butyl peradipate, di-t-butyl perazelate, di-t-butyl perglutarate, di-t-butyl perthalate, di-t-butyl persebacate, 4-nitrocumyl perpropionate, 1-phenylethyl perbenzoate, phenylethyl nitro-perbenzoate, t-butylbicyclo-(2,2,1)heptane percarboxylate, t-butyl-4-carbomethoxy perbutyrate, t-butylcyclobutane percarboxylate, t-butylcyclohexyl peroxycarboxylate, t-butylcyclopentyl percarboxytate, t-butylcyclopropane percarboxylate, t-butyldimethyl percinnamate, t-butyl-2-(2,2-diphenylvinyl) perbenzoate t-butyl-4-methoxy perbenzoate, t-butylperbenzoate, t-butylcarboxycyclohexane, t-butylpernaphthoate, t-butyl eroxyisopropylcarbonate, t-butyl pertoluate, t-butyl-1-phenylcyclopropyl percarboxylate, t-butyl-2-propylperpentene-2-oate, t-butyl-1-methylcyclopropy percarboxylate, t-butyl-4-nitrophenyl peracetate, t-butylnitrophenyl peroxycarbamate, t-butyl-N-succiimido percarboxylate, t-butyl percrotonate, t-butyl permaleic acid, t-butyl permethacrylate, t-butyl peroctoate, t-butyl peroxyisopropylcarbonate, t-butyl perisobutyrate, t-butyl peracrylate and/or t-butyl perpropionate;

or mixtures of these above listed free radical-forming agents.

If present in the process for the manufacture of the polypropylene (A), the (volatile) bifunctional monomers are preferably ethylenically unsaturated, multifunctional monomers, like C4 to C10 dienes and/or C7 to C10 divinyl compounds. Especially preferred bifunctional monomers are butadiene, isoprene, dimethylbutadiene and divinylbenzene.

The polypropylene (A) is preferably obtained by a process as described in EP 0 879 830 A 1 and EP 0 890 612 A2. Both documents are herewith included by reference. Accordingly the polypropylene is produced by
(a) mixing
  (i) a unmodified propylene homopolymer and/or copolymer (A') as defined above, preferably a unmodified propylene homopolymer with a weight average molecular weight ($M_w$) of 500,000 to 1,500,000 g/mol,
  (ii) from 0.05 to 3 wt.-% based on the components of (i) and (ii), of a peroxide selected from the group consisting of acyl peroxide, alky peroxide, hydroperoxide, perester and peroxycarbonate, and,
  (iii) optionally diluted with inert solvents,
(b) heating to 30-100° C., preferably to 60-90° C.,
(c) sorption of volatile bifunctional monomers, preferably ethylenically unsaturated, multifunctional monomers, like C4 to C10 dienes and/or C7 to C10 divinyl compounds, by the unmodified propylene homopolymer and/or copolymer (A), preferably unmodified propylene homopolymer (A), from the gas phase at a temperature of from 20 to 120° C.1 preferably of from 60 to 100° C., where the amount of the absorbed bifunctionally unsaturated monomers is from 0.01 to 10.00 wt.-%, preferably from 0.05 to 2.00 wt.-%, based on the propylene homopolymer (A'),
(d) heating and melting the polypropylene composition in an atmosphere comprising inert gas and/or the volatile bifunctional monomers, from sorption temperature to 210° C., whereupon the free-radical generators are decomposed and then
(e) heating the melt up to 280° C. in order to remove unreacted monomers and decomposition products, and
(f) agglomerating the melt.

Usual amounts of auxiliary substances, which may range from 0.01 to 2.5% by weight of stabilizers, 0.01 to 1% by weight of processing aids, 0.1 to 1% by weight of antistats, 0.2 to 3% by weight of pigments and up to 3% by weight of α-nucleating agents, in each case based on the sum of the propylene polymers, may be added before step a) and/or f) of the method and/or before or during step d) and/or e) of the above described method.

The process for producing the modified propylene polymer preferably is a continuous method, performed in continuous reactors, mixers, kneaders and extruders. Batchwise production of the modified propylene polymer however is feasible as well.

Practical sorption times τ of the volatile bifunctional monomers range from 10 to 1000 s, where sorption times τ of 60 to 600 are preferred.

Polypropylene (A) can also be produced in the presence of a metallocene catalyst, as, for example, described in EP 1 892 264 •using a catalyst system comprising an asymmetric catalyst, whereby the catalyst system has a porosity of less than 1.40 ml/g, more preferably less than 1.30 ml/g and most preferably less than 1.00 ml/g. The porosity has been measured according to DIN 66135 ($N_2$). In another preferred embodiment the porosity is not detectable when determined with the method applied according to DIN 66135 ($N_2$).

An asymmetric catalyst is a metallocene compound comprising at least two organic ligands which differ in their chemical structure. More preferably the asymmetric catalyst is a metallocene compound comprising at least two organic ligands which differ in their chemical structure and the metallocene compound is free of $C_2$-symmetry and/or any higher symmetry. Preferably the asymmetric metallocene compound comprises only two different organic ligands, still more preferably comprises only two organic ligands which are different and linked via a bridge.

Said asymmetric catalyst is preferably a single site catalyst (SSC).

Furthermore it is preferred, that the catalyst system has a surface area of less than 25 $m^2$/g, yet more preferred less than 20 $m^2$/g, still more preferred less than 15 $m^2$/g, yet still less than 10 $m^2$/g and most preferred less than 5 $m^2$/g. The surface area according to this invention is measured according to ISO 9277 ($N_2$).

It is in particular preferred that the catalytic system comprises an asymmetric catalyst, i.e. a catalyst as defined below, and has porosity not detectable when applying the method according to DIN 66135 ($N_2$) and has a surface area measured according to ISO 9277 ($N_2$) less than 5 $m^2$/g.

Preferably the asymmetric catalyst compound, i.e. the asymmetric metallocene, has the formula (1):

$$(Cp)_2 R_z M X_2 \qquad (I)$$

wherein
z is 0 or 1,
M is Zr, Hf or Ti, more preferably Zr, and
X is independently a monovalent anionic ligand, such as σ-ligand
R is a bridging group linking the two Cp ligands
Cp is an organic ligand selected from the group consisting of unsubstituted cyclopentadienyl, unsubstituted indenyl, unsubstituted tetrahydroindenyl, unsubstituted fluorenyl, substituted cyclopentadienyl, substituted indenyl, substituted tetrahydroindenyl, and substituted fluorenyl, with the proviso that both Cp-ligands are selected from the above stated group and both Cp-ligands have a different chemical structure.

The term "σ-ligand" is understood in the whole description in a known manner, i.e. a group bonded to the metal at one or more places via a sigma bond. A preferred monovalent anionic ligand is halogen, in particular chlorine (Cl).

Preferably, the asymmetric catalyst is of formula (I) indicated above, wherein
M is Zr and
each X is Cl.

Preferably both identical Cp-ligands are substituted.
Preferably both Cp-ligands have different residues to obtain an asymmetric structure.

Preferably, both Cp-ligands are selected from the group consisting of substituted cyclopentadienyl-ring, substituted indenyl-ring, substituted tetrahydroindenyl-ring, and substituted fluorenyl-ring wherein the Cp-ligands differ in the substituents bonded to the rings.

The optional one or more substituent(s) bonded to cyclopentadienyl, indenyl, tetrahydroindenyl, or fluorenyl may be independently selected from a group including halogen hydrocarbyl (e.g. $C_1$-$C_{20}$-alkyl, $C_2$-$C_{20}$-alkenyl, $C_2$-$C_{20}$-alkynyl, $C_3$-$C_{12}$-cycloalkyl, $C_6$-$C_{20}$-aryl or $C_7$-$C_{20}$-arylalkyl), $C_3$-$C_{12}$-cycloalkyl which contains 1, 2, 3 or 4 heteroatom(s) in the ring moiety, $C_6$-$C_{20}$-heteroaryl, $C_1C_{20}$-haloalkyl, —$SiR''_3$, —$OSiR''_3$, —$SR''$, —$PR''_2$ and —$NR''_2$, wherein each R'' is independently a hydrogen or hydrocarbyl, e.g. $C_1$-$C_{20}$-alkyl, $C_2$-$C_{20}$-alkenyl, $C_2$-$C_{20}$-alkynyl, $C_3$-$C_{12}$-cycloalkyl or $C_6$-$C_{20}$-aryl.

More preferably both Cp-ligands are indenyl moieties wherein each indenyl moiety bear one or two substituents as defined above. More preferably each Cp-ligand is an indenyl moiety bearing two substituents as defined above, with the proviso that the substituents are chosen in such are manner that both Cp-ligands are of different chemical structure, i.e. both Cp-ligands differ at least in one substituent bonded to the indenyl moiety, in particular differ in the substituent bonded to the five member ring of the indenyl moiety.

Still more preferably both Cp are indenyl moieties wherein the indenyl moieties comprise at least at the five membered ring of the indenyl moiety, more preferably at 2-position, a substituent selected from the group consisting of alkyl, such as $C_1$-$C_6$ alkyl, e.g. methyl, ethyl, isopropyl, and trialkyloxysiloxy, wherein each alkyl is independently selected from $C_1$-$C_6$ alkyl, such as methyl or ethyl, with proviso that the indenyl moieties of both Cp must chemically differ from each other, i.e. the indenyl moieties of both Cp comprise different substituents.

Still more preferred both Cp are indenyl moieties wherein the indenyl moieties comprise at least at the six membered ring of the indenyl moiety, more preferably at 4-position, a substituent selected from the group consisting of a $C_6$-$C_{20}$ aromatic ring moiety, such as phenyl or naphthyl, preferably phenyl, which is optionally substituted with one or more substituents, such as $C_1$-$C_6$ alkyl, and a heteroaromatic ring moiety, with proviso that the indenyl moieties of both Cp must chemically differ from each other, i.e. the indenyl moieties of both Cp comprise different substituents.

Yet more preferably both Cp are indenyl moieties wherein the indenyl moieties comprise at the five membered ring of the indenyl moiety, more preferably at 2-position, a substituent and at the six membered ring of the indenyl moiety, more preferably at 4-position, a further substituent, wherein the substituent of the five membered ring is selected from the group consisting of alkyl, such as $C_1$-$C_6$ alkyl, e.g. methyl, ethyl, isopropyl, and trialkyloxysiloxy, wherein each alkyl is independently selected from $C_1$-$C_6$ alkyl, such as methyl or ethyl, and the further substituent of the six membered ring is selected from the group consisting of a $C_6$-$C_{20}$ aromatic ring moiety, such as phenyl or naphthyl, preferably phenyl, which is optionally substituted with one or more substituents, such as $C_1$-$C_6$ alkyl, and a heteroaromatic ring moiety, with proviso that the indenyl moieties of both Cp must chemically differ from each other, i.e. the indenyl moieties of both Cp comprise different substituents. It is in particular preferred that both Cp are idenyl rings comprising two substituents each and differ in the substituents bonded to the five membered ring of the idenyl rings.

Concerning the moiety "R" it is preferred that "R" has the formula (II)

$$—Y(R')_2— \tag{II}$$

wherein
Y is C, Si or Ge, and
R' is $C_1$ to $C_{20}$ alkyl $C_6$-$C_{12}$ aryl, or $C_7$-$C_{12}$ arylalkyl or trimethylsilyl.

In case both Cp-ligands of the asymmetric catalyst as defined above, in particular case of two indenyl moieties, are linked with a bridge member R, the bridge member R is typically placed at 1-position. The bridge member R may contain one or more bridge atoms selected from e.g. C, Si and/or Ge, preferably from C and/or Si. One preferable bridge R is —$Si(R')_2$—, wherein R' is selected independently from one or more of e.g. trimethylsilyl, $C_1$-$C_{10}$ alkyl, $C_1$-$C_{20}$ alkyl, such as $C_6$-$C_{12}$ aryl, or $C_7$-$C_{40}$, such as $C_7$-$C_{12}$ arylalkyl, wherein alkyl as such or as part of arylalkyl is preferably $C_1$-$C_6$ alkyl, such as ethyl or methyl, preferably methyl, and aryl is preferably phenyl. The bridge —$Si(R')_2$— is preferably e.g. —$Si(C_1$-$C_6$ alkyl$)_2$-, —$Si(phenyl)_2$- or —$Si(C1$-$C6$ alkyl)(phenyl)-, such as —$Si(Me)_2$-.

In a preferred embodiment the asymmetric catalyst, i.e. the asymmetric metallocene, is defined by the formula (III).

$$(Cp)_2R_1ZrCl_2 \tag{III}$$

wherein
both Cp coordinate to M and are selected from the group consisting of unsubstituted cyclopentadienyl, unsubstituted indenyl, unsubstituted tetrahydroindenyl, unsubstituted fluorenyl, substituted cyclopentadienyl, substituted indenyl, substituted tetrahydroindenyl, and substituted fluorenyl,
with the proviso that both Cp-ligands are of different chemical structure, and R is a bridging group linking two ligands L,
wherein R is defined by the formula (II)

$$—Y(R')_2— \tag{II}$$

wherein
Y is C, Si or Ge, and
R' is $C_1$ to $C_{20}$ alkyl, $C_6$-$C_{12}$ aryl, or $C_7$-$C_{12}$ arylalkyl.

More preferably the asymmetric catalyst is defined by the formula (III), wherein both Cp are selected from the group consisting of substituted cyclopentadienyl, substituted indenyl, substituted tetrahydroindenyl, and substituted fluorenyl.

Yet more preferably the asymmetric catalyst is defined by the formula (III), wherein both Cp are selected from the group consisting of substituted cyclopentadienyl, substituted indenyl, substituted tetrahydroindenyl, and substituted fluorenyl with the proviso that both Cp-ligands differ in the substituents, i.e. the substituents as defined above, bonded to cyclopentadienyl, indenyl, tetrahydroindenyl, or fluorenyl.

Still more preferably the asymmetric catalyst is defined by the formula (III), wherein both Cp are indenyl and both indenyl differ in one substituent, i.e. in a substituent as defined above bonded to the five member ring of indenyl.

It is in particular preferred that the asymmetric catalyst is a non-silica supported catalyst as defined above, in particular a metallocene catalyst as defined above.

In a preferred embodiment the asymmetric catalyst is dimethylsilyl [(2-methyl-(4'-tert.butyl)-4-phenyl-indenyl)(2-isopropyl-(4'-tert.butyl)-4-phenyl-indenyl)]zirkonium dichloride (IUPAC: dimethylsilandiyl [(2-methyl-(4'-tert. butyl)-4-phenyl-indenyl)](2-isopropyl-(4'-tert.butyl)-4-phenyl-indenyl)]zirkonium dichloride). More preferred said asymmetric catalyst is not silica supported.

The above described asymmetric catalyst components are prepared according to the methods described in WO 01/48034.

It is in particular preferred that the asymmetric catalyst system is obtained by the emulsion solidification technology as described in WO 03/051934. This document is herewith included in its entirety by reference. Hence the asymmetric catalyst is preferably in the form of solid catalyst particles, obtainable by a process comprising the steps of
- a) preparing a solution of one or more asymmetric catalyst components;
- b) dispersing said solution in a solvent immiscible therewith to form an emulsion in which said one or more catalyst components are present in the droplets of the dispersed phase,
- c) solidifying said dispersed phase to convert said droplets to solid particles and optionally recovering said particles to obtain said catalyst.

Preferably a solvent, more preferably an organic solvent, is used to form said solution. Still more preferably the organic solvent is selected from the group consisting of a linear alkane, cyclic alkane, linear alkene, cyclic alkene, aromatic hydrocarbon and halogen-containing hydrocarbon.

Moreover the immiscible solvent forming the continuous phase is an inert solvent, more preferably the immiscible solvent comprises a fluorinated organic solvent and/or a functionalized derivative thereof, still more preferably the immiscible solvent comprises a semi-, highly- or perfluorinated hydrocarbon and/or a functionalized derivative thereof. It is in particular preferred, that said immiscible solvent comprises a perfluorohydrocarbon or a functionalized derivative thereof, preferably $C_3$-$C_{30}$ perfluoroalkanes, -alkenes or -cycloalkanes, more preferred $C_4$-$C_{10}$ perfluoroalkanes, -alkenes or -cycloalkanes, particularly preferred perfluorohexane, perfluoroheptane, perfluorooctane or perfluoro(methylcyclohexane) or a mixture thereof.

Furthermore it is preferred that the emulsion comprising said continuous phase and said dispersed phase is a bi- or multiphasic system as known in the art. An emulsifier may be used for forming the emulsion. After the formation of the emulsion system, said catalyst is formed in situ from catalyst components in said solution.

In principle, the emulsifying agent may be any suitable agent which contributes to the formation and/or stabilization of the emulsion and which does not have any adverse effect on the catalytic activity of the catalyst. The emulsifying agent may e.g. be a surfactant based on hydrocarbons optionally interrupted with (a) heteroatom(s), preferably halogenated hydrocarbons optionally having a functional group, preferably semi-, highly- or perfluorinated hydrocarbons as known in the art. Alternatively, the emulsifying agent may be prepared during the emulsion preparation, e.g. by reacting a surfactant precursor with a compound of the catalyst solution. Said surfactant precursor may be a halogenated hydrocarbon with at least one functional group, e.g. a highly fluorinated $C_1$ to $C_{30}$ alcohol, which reacts e.g. with a cocatalyst component, such as aluminoxane.

In principle any solidification method can be used for forming the solid particles from the dispersed droplets. According to one preferable embodiment the solidification is effected by a temperature change treatment. Hence the emulsion subjected to gradual temperature change of up to 10° C./min, preferably 0.5 to 6° C./min and more preferably 1 to 5° C./min. Even more preferred the emulsion is subjected to a temperature change of more than 40° C., preferably more than 50° C. within less than 10 seconds, preferably less than 6 seconds.

The recovered particles have preferably an average size range of 5 to 200 μm, more preferably 10 to 100 μm.

Moreover, the form of solidified particles have preferably a spherical shape, a predetermined particles size distribution and a surface area as mentioned above of preferably less than 25 m$^2$/g, still more preferably less than 20 m$^2$/g, yet more preferably less than 15 m$^2$/g, yet still more preferably less than 10 m$^2$/g and most preferably less than 5 m$^2$/g, wherein said particles are obtained by the process as described above.

For further details, embodiments and examples of the continuous and dispersed phase system, emulsion formation method, emulsifying agent and solidification methods reference is made e.g. to the above cited international patent application WO 03/051934.

As mentioned above the catalyst system may further comprise an activator as a cocatalyst, as described in WO 03/051934, which is enclosed herein with reference.

Preferred as cocatalysts for metallocenes and non-metallocenes, if desired, are the aluminoxanes, in particular the $C_1$-$C_{10}$-alkylaluminoxanes, most particularly methylatuminoxane (MAO). Such aluminoxanes can be used as the sole cocatalyst or together with other cocatalyst(s). Thus besides or in addition to aluminoxanes, other cation complex forming catalysts activators can be used. Said activators are commercially available or can be prepared according to the prior art literature.

Further aluminoxane cocatalysts are described i.a. in WO 94/28034 which is incorporated herein by reference. These are linear or cyclic oligomers of having up to 40, preferably 3 to 20, —(Al(R''')O)— repeat units (wherein R''' is hydrogen, $C_1$-$C_{10}$-alkyl (preferably methyl) or $C_6$-$C_{18}$-aryl or mixtures thereof).

The use and amounts of such activators are within the skills of an expert in the field. As an example, with the boron activators, 5:1 to 1:5, preferably 2:1 to 1:2, such as 1:1, ratio of the transition metal to boron activator may be used. In case of preferred aluminoxanes, such as methylaluminumoxane (MAO), the amount of Al, provided by aluminoxane, can be chosen to provide a molar ratio of Al:transition metal e.g. in the range of 1 to 10 000, suitably 5 to 8000, preferably 10 to 7000, e.g. 100 to 4000, such as 1000 to 3000. Typically in case of solid (heterogeneous) catalyst the ratio is preferably below 500.

The quantity of cocatalyst to be employed in the catalyst of the invention is thus variable, and depends on the conditions and the particular transition metal compound chosen in a manner well known to a person skilled in the art.

Any additional components to be contained in the solution comprising the organotransition compound may be added to said solution before or, alternatively, after the dispersing step.

The process for producing polypropylene (A) using the above defined metallocene catalyst is a multi-stage process.

Multistage processes include also bulk/gas phase reactors known as multizone gas phase reactors for producing multimodal propylene polymer.

A preferred multistage process is a "loop-gas phase"-process, such as developed by Borealis A/S, Denmark (known as BORSTAR® technology) described e.g. in patent literature, such as in EP 0 887 379 or in WO 92/12182.

Multimodal polymers can be produced according to several processes which are described, e.g. in WO 92/12182, EP 0 887 379 and WO 97/22633.

A multimodal polypropylene (A) is produced preferably in a multi-stage process in a multi-stage reaction sequence as described in WO 92/12182. The contents of this document are included herein by reference.

The second component of the composition can be selected from the group of
(i) maleic anhydride-modified polypropylene (MAPP)
(ii) maleic anhydride-modified polypropylene wax
(iii) polypropylene homopolymer with high melt flow rate or
(iv) ethylene-vinyl acetate-based hot melt adhesive Ad (i) Maleic Anhydride-Modified Polypropylene (MAPP):

The graft modification of polymers with various olefinically unsaturated monomers is well known in the art and numerous commercially available graft modified maleic anhydride polymers are available.

The graft-modified polypropylene (i) used in the present invention is a polypropylene modified by partially or wholly grafting with maleic anhydride.

The propylene used for graft modification is a homopolymer of propylene and/or a random copolymer of propylene and an alpha-olefin containing constituent units derived from the alpha-olefin other than propylene in amounts of not more than 10% by mole based on 100% by mol of the total of constituent units derived from propylene and constituent units derived from an alpha-olefin other than propylene. Ethylene and/or an alpha-olefin having 4 to 20 carbon atoms, including 1-butene, 1-pentene, 1-hexene, 1-heptene, 1-octene, 1-nonene, 1-decene and 4-methyl-1-pentene, are used as the alpha-olefin in the propylene, either singly or in combination of two or more kinds.

In the propylene/alpha-olefin random copolymer, constituent units derived from propylene are contained in amounts of not less than 90% by mol, usually 90 to 99% by mol, preferably not less than 96% by mol, and constituent units derived from ethylene or an alpha-olefin of 4 to 20 carbon atoms are contained in amounts of not more than 10% by mol, usually 1 to 10% by mol, preferably not more than 6% by mol.

Examples of propylene/alpha-olefin random copolymers include a propylene/ethylene copolymer, a propylene/1-butene copolymer, a propylene/ethylene/1-butene copolymer and a propylene/ethylene/1-octene copolymer.

Preferably a random copolymer of propylene with ethylene is used.

The production method of the polypropylene used for graft modification in the present invention is not particularly limited. The polypropylene may be produced by using well-known catalysts such as Ziegler-Natta catalysts or a metallocene catalyst with well-known processes.

In the modified polypropylene, a part or the whole of propylene (a propylene homopolymer or a propylene/alpha-olefin random copolymer) is graft modified with maleic anhydride in an amount of preferably $10^{-8}$ to $10^{-2}$ g equivalent, more preferably $10^{-7}$ to $10^{-3}$ g equivalent, based on 1 g of the polypropylene before the graft modification. That is, the modified polypropylene may partly include unmodified polypropylene. When the modified polypropylene for use in the invention contains unmodified polypropylene, the content of the unmodified polypropylene is desired to be not more than 95 parts per weight, usually 85 to 40 parts by weight, based on 100 parts by weight of the total of the graft modified polypropylene and the unmodified polypropylene.

The method of graft modification of the propylene with maleic anhydride is not particularly limited and can be carried out by well-known graft polymerization methods such as a solvent method or a melt kneading method. For example, a method of performing graft reaction by adding the graft monomer maleic anhydride to a molten polymer or a method of performing graft reaction by dissolving a polymer in a solvent to make a solution to which the graft monomer is added may be employed.

When the graft polymerization is carried out in the presence of a radical initiator in the above processes, the graft monomer maleic anhydride can be efficiently graft polymerized. In this case, the radical initiator is used in an amount of usually 0.001 to 1 part per weight based on 100 parts per weight of the polypropylene. The radical initiators used herein are, for example, an organic peroxide or an azo compound.

Specific examples of the radical initiators include benzoyl peroxide, lauroyl peroxide, dichlorobenzoyl peroxide, dicumyl peroxide, di-t-butyl peroxide, 2,5-dimethyl-2,5-di (t-butylperoxide)hexyne-3,2,5-dimethyl-2,5-di-(t-butylperoxide)-hexane, 1,4-bis(t-butylperoxyisopropyle)benzene, azobisisobutyronitrile, etc.

The reaction temperature of the graft polymerization reaction using a radical initiator or the graft polymerization using no radical initiator is set in the range of usually 60 to 350° C., preferably 150° C. to 300° C.

The content of the maleic anhydride can be easily controlled, for example, by suitable selection of the grafting conditions.

The content of maleic anhydride in the graft-modified polypropylene used in the present invention is in the range of 0.001 to 10 wt %, preferably 0.01 to 5 wt %, more preferably 0.02 to 4 wt %.

The graft modified polypropylene has normally a melt flow rate (MFR) measured according to ISO 1133 at 230° C. under a load of 2.16 kg of 0.01 to 1000 g/10 min, preferably 0.1 to 500 g/10 min, more preferably 1.0 to 50 g/10 min.

The anhydride modified polypropylene used in the present invention is preferably a modification product obtained by grafting maleic anhydride on a homopolymer of propylene or a propylene/ethylene random copolymer. More preferably the MAPP used according to the invention is a maleic anhydride modified propylene/ethylene random copolymer.

Examples of commercially available modified polypropylene products that can suitably be employed in the present invention are Priex® 25097 by Solvay, Hercoprime™ G-211 by Himont Inc., Admer® AT2059E by Mitsui Chemicals, Bynel® 50E803 by DuPont, Exxelor PO 1020 by Exxon-Mobil, Polybond® 3200 by Crompton, Scona® TPPP 2112 F by Kometra, and the like.

Ad (ii) Maleic Anhydride-Modified Polypropylene Wax

Suitable maleic anhydride-modified propylene waxes include homopolymers of propylene or copolymers of propylene with ethylene or one or more 1-olefins produced in the presence of a Ziegler-Natta or metallocene catalyst and subsequently grafted with maleic anhydride.

1-olefins used include linear or branched olefins having 4 to 18 carbon atoms, preferably 4 to 10 carbon atoms. These olefins may have an aromatic substitution which is in conjugation with the olefinic double bond. Examples of such compounds are 1-butene, 1-hexene, 1 octene or 1-octadecen and also styrene. Preference is given to propylene homopolymers or propylene copolymers with ethylene.

Especially suitable modified polypropylene waxes are those having a softening point Ts (ring/ball) from 85 to 165° C., a melt viscosity, measured at a temperature 10° C. above Ts, of between 20 and 40 000 mPa·s, preferably between 50 and 10.000 mPa·s and a density at 23° C. between 0.89 and 0.96 g/cm$^3$, preferably between 0.91 and 0.94 g/cm$^3$.

The weight average molecular weight (Mw) of the polypropylene waxes used for being grafted is preferably of less than 10.000 g/mol, more preferably in the range of 500 to 10.000 g/mol, still more preferably in the range of 1.000 to 9.000 g/mol.

The fraction of the polar graft comonomer (maleic anhydride), based on grafted polypropylene wax is preferably 0.1 wt % to 20 wt %.

In a preferred embodiment of the present invention the grafted polypropylene wax has a high degree of grafting, i.e. high content of maleic anhydride in the graft-modified polypropylene wax used in the present invention.

The acid number of the modified propylene wax is from 0.5 to 120 mg KOH/g, preferably from 1 to 60 mg KOH/g, more preferably from 2 to 40 mg KOH/g.

The acid number is defined as the number of milligrams of KOH which are required to neutralize one gram of sample. Acid numbers were obtained by titrating weighed samples dissolved in refluxing xylene with methanolic potassium hydroxide using phenolphthalein as an indicator. End points were taken when the pink color of the indicator remained 10 seconds.

The synthesis of the unmodified, i.e. nonpolar, starting waxes by means of catalysts of the Ziegler or metallocene type is known from numerous documents. Thus, for example, DE-A-2329641 discloses a process by means of which α-olefins can be polymerized in a direct polymerization reaction using Ziegler catalysts to give homopolymer or copolymer waxes. DE-A-3148229 describes the preparation of highly crystalline polypropylene waxes by polymerization likewise using titanium-containing catalysts; the same in EP-A480190. In addition, propylene homopolymer and copolymer waxes are also obtainable using metallocene catalysts (e.g. U.S. Pat. No. 6,331,590, EP-A-321 852, EP-A-384 26, EP-A416 566 or EP 571 882).

Suitable starting materials are low molecular weight propylene homopolymers prepared using Ziegler or metallocene catalysts and having melt viscosities, measured at a temperature 10° C. above Ts, of from 20 to 50 000 mPa·s. The softening points (ring/ball) of such waxes are generally from 90 to 165° C. Suitable waxes are both highly crystalline products having a high proportion of isotactic or syndiotactic structures and those having a low crystallinity and a predominantly atactic structure. The degree of crystallinity of propylene homopolymers can be varied within wide limits in a known manner by appropriate selection of the catalyst used for the polymerization and by means of the polymerization conditions. This applies particularly when using metallocene catalyst systems.

Further suitable starting materials are propylene copolymer waxes which are prepared using Ziegler or metallocene catalysts and comprise not only propylene but also varying amounts of other olefins, for example ethylene or higher α-olefins having a chain length range of $C_4$-$C_{30}$, where the comonomer units can be distributed either predominantly randomly or predominantly in blocks between isotactic, syndiotactic or partially atactic polypropylene sequences. Such waxes have softening points (ring/ball) of generally from about 90 to 165° C.

Preferably unmodified polypropylene waxes prepared in the presence of a metallocene catalyst are used for being grafted with maleic acid.

The grafting process can be performed as described for component (i), according to well-known processes. For example, grafting with maleic anhydride may be performed for example according to U.S. Pat. No. 5,998,547, U.S. Pat. No. 6,569,950 or EP 0 941 257.

The reaction of the polypropylene wax with maleic anhydride can be carried out either continuously or batchwise. In the batchwise procedure, the wax is heated to a temperature above its softening point and maleic anhydride and a peroxide, as described above, are introduced into the melt while stirring, either continuously over an appropriate period of time or in one or more portions, if desired under a blanket of inert gas. The reaction temperature is above the softening point of the wax, preferably from 100 to 200° C., particularly preferably from 130 to 180° C. After metering-in is complete, the mixture can be left to react further at the same temperature or a different temperature, if desired after addition of a further amount of peroxide. Volatile components formed during the reaction or excess volatile starting components can, for example, be distilled off under reduced pressure or be removed by stripping with inert gas.

Examples of commercially available modified polypropylene products that can suitably be employed in the present invention are Licocene® PP MA 7452, Licocene® PP MA 6252 TP, Licocene® PP MA 6452, Licocene® PP MA 1332 TP, Licocene® PP MA 1452 all by Clariant, Epolene E-43 by Eastman, and the like.

(iii) Polypropylene Homopolymer with High Melt Flow Rate

According to the present invention polypropylene homopolymers with high melt flow rate can also be used as component B.

The polymers that can be suitably be employed have a melt flow rate (MFR) measured according to ISO 1133 at 230° C. under a load of 2.16 kg of from 50 to 3000 g/10 min, preferably from 100 to 2000 g/10 min, more preferably from 200 to 1500 g/10 min.

The expression homopolymer used in the instant invention relates to a polypropylene that consists substantially, i.e. of at least 97 wt %, preferably of at least 99 wt %, and most preferably of at least 99.8 wt % of propylene units. In a preferred embodiment only propylene units in the propylene homopolymer are detectable. The comonomer content can be determined with FT infrared spectroscopy, as described below in the examples.

The high melt flow rate polypropylenes used according to the invention can be produced directly in a polymerization reactor by well-known processes, described in several patent applications (for example in EP 0 320 150, EP 0 480 190, EP 0 622 380, EP 1 303 547, EP 1 538 167, EP 1 783 145, WO 2007/140019, etc.).

Alternatively the high melt flow rate polypropylenes used according to the invention can be obtained by controlled rheology (CR) techniques, including, e.g., visbreaking, which means that a polymer, having low melt flow rate, is subjected to a post-reactor treatment, wherein the polymer molecules are subjected to controlled scission in molten state. The scission may be carried out by mechanical shearing, radiation and oxidation or chemically with peroxy compounds.

Preferably controlled rheology treatments are carried out using organic peroxides.

The process of visbreaking a propylene polymer material is well known to those skilled in the art and is described in several patent applications (for example in U.S. Pat. No. 3,940,379, U.S. Pat. No. 4,951,589, U.S. Pat. No. 4,282,076, U.S. Pat. No. 5,250,631, EP 0 462 574, WO 02/096986, WO 2004/113438.

The polymer used as starting compound for the controlled rheology treatment may be produced by any polymerisation process known in the art.

The polymerisation process may be a continuous process or a batch process utilizing known methods and operating in liquid phase, optionally in the presence of an inert diluent, or in gas phase or by mixed liquid-gas techniques. The process is preferably carried out in the presence of a stereospecific catalyst system.

As catalyst any ordinary stereospecific Ziegler-Natta catalysts or any metallocene catalyst capable of catalysing the formation of a propylene polymer can be used.

In addition, examples of commercially available modified polypropylene products that can suitably be employed in the present invention are Borflow™ HL504FB, HL508FB or HL512FB all by Borealis, Metocene MF650 by Basell Polyolefins, Marlex® HGZ-1200 by Phillips Sumika Polypropylene Company, Escorene™ PP3505 and PP3746 all by ExxonMobile, EOD 96-36 and 3960X by Fina, Valtec grades like HH442H, HH441, PF008, PF0171 etc. by LyondellBasell etc.

(iv) Ethylene-Vinyl Acetate-Based Hot Melt Adhesive

A hot melt adhesive is generally manufactured from a mixture of three components: a thermoplastic resin, a tackifying agent, and paraffin or a microcrystalline polymeric wax. The thermoplastic resins commonly used in compositions for the manufacture of hot melt adhesives have included copolymers of ethylene and vinyl esters, particularly vinyl acetate, or copolymers of ethylene and alkyl acrylates, particularly ethyl acrylate and butyl acrylate.

According to the present invention hot melt adhesives based on ethylene-vinyl acetate copolymers can be used as component B.

Various formulations including ethylene-vinyl acetate (EVA) copolymers are known in the art.

Ethylene-vinyl acetate (EVA) copolymers are conventionally regarded as those copolymers of ethylene and vinyl acetate where the weight percentage of ethylene in the polymer molecule exceeds that of the vinyl acetate.

The ethylene-vinyl acetate copolymers (EVA) useful herein are those containing at least about 15 to 45 wt % vinyl acetate and having a melt index (ISO 1133, 190° C., 2.16 kg) in the range of 2 to 2500 g/10 min. The EVA copolymers will preferably comprise less than 40 weight percent vinyl acetate (VA), although EVA copolymers are nowadays available with a vinyl acetate content of above 50 wt %.

Useful commercially available ethylene-vinyl acetate copolymers are for example ATEVA® grades from AT Plastics Inc., Brampton, Ontario, Escruene® grades from ExxonMobile, Elvax® grades from Dupont, Evatane® grades, for example supplied by Atofina, and the like.

Useful commercially available hot melt adhesives based on ethylene-vinyl acetate copolymers that can suitably be employed in the present invention are for example Sitomelt® grades like K 608/1 from Kiilto OY, Quicklock Hotmelt CH 155 supplied by Chemline India Ltd., 3M™ Jet-melt™ hot melt adhesive grades, etc.

The two component adhesion compositions according to the present invention comprise a) 70 to 98 wt % of component (A), described in detail above and b) 2 to 30 wt % of component (B), described in detail above.

Preferably the two component adhesion compositions according to the present invention comprise a) 75 to 95 wt % of component (A) and b) 5 to 25 wt % of component (B).

As component (B) preferably one compound selected from the group of
(i) maleic anhydride-modified polypropylene (MAPP)
(ii) maleic anhydride-modified polypropylene wax or
(iv) ethylene-vinylacetat based hot metal adhesive
all described in detail above, is used.

More preferably component (B) is (i) a maleic anhydride-modified polypropylene (MAPP) or (ii) a maleic anhydride-modified polypropylene wax and still more preferably component (B) is a maleic anhydride-modified polypropylene wax.

The adhesive composition in accordance with the present invention may furthermore comprise small amounts of additional, conventional components (additives), commonly used and well known in the adhesive art. The type and amount of such additives can be selected by the skilled person on the basis of the general knowledge in the art. Typically these additive do not amount to more than 5 wt.-% (in total), based on the adhesive composition.

The adhesive composition may be prepared in a usual manner, including blending the individual components using appropriate devices, such as kneaders and extruders.

Thus the highly adhesive composition of the present invention may be prepared by mixing the two components and optionally one or more additives, as described above, to form a blend and then melt kneading the resulting mixture.

The melt-kneading may be carried out using a kneading machine, such as a mixing roll, a Branbury mixer, a kneader, or a single-screw or twin-screw extruder.

The adhesive composition according to the present invention has particular utility as a coating for paper substrates Any types of papers conventionally known in the art for preparing coated papers can be used, such as but not limited to kraft paper, natural or synthetic pulp paper, paper board, liner board and the like. The paper may further be bleached and/or coated.

The adhesive composition in accordance with the present invention is in particular suitable for coating by extrusion processes.

The extrusion coating process may be carried out using conventional extrusion coating techniques.

Hence, the adhesive composition according to the present invention is fed, typically in the form of pellets, optionally containing additives, to an extruding device. From the extruder the polymer melt is passed preferably through a flat die to the substrate to be coated. Due to the distance between the die lip and the nip, the molten plastic is oxidized in the air for a short period, usually leading to an improved adhesion between the coating and the substrate. The coated substrate is cooled on a chill roll, after which it is passed to edge trimmers and wound up. The width of the line may vary between, for example, 500 to 1500 mm, e. g. 800 to 1100 mm, with a line speed of up to 1000 m/min, for instance 300 to 800 m/min. The temperature of the polymer melt is typically between 275 and 330° C. The polypropylene of the invention can be extruded onto the substrate as a monolayer coating or as one layer in coextrusion. In a multilayer extrusion coating, the other layers may comprise any polymer resin having the desired properties and processability.

Therefore, a further object of the invention is the use of the polypropylene composition in extrusion coating processes using paper, as defined above, as substrate.

The composition of the present invention is highly adhesive and thus none of the methods commonly known in the art to improve adhesion between the paper substrate and the polypropylene layer produced from the composition according to the invention, such as ozone treatment of the molten polymer film, corona treatment of the substrate and use of a coextruded adhesion layer need to be applied.

Nevertheless it is possible to perform ozone and/or corona treatment in a known way, if desired or necessary.

The main end-uses for extrusion coated products obtained by using the adhesive composition according to the invention are in packaging applications, like liquid packaging for milk, juice, wine or other liquids, flexible packaging for meat, cheese and medical products, rigid packaging like detergent cartons, cup and plate boards for oven or microwave use or sterilizable food packaging, but also for photographic paper or industrial applications like paper reel and ream wraps.

The present invention, as outlined above, therefore also provides a substrate, respectively article which has at least one layer of highly adherent propylene polymer composition according to the invention on at least one surface.

Furthermore the present invention is also directed to the use of the inventive article as packaging material, in particular as a packaging material for food and/or medical products.

In the following, the present invention is described by way of examples.

DEFINITIONS/MEASURING METHODS

The following definitions of terms and determination methods apply for the above general description of the invention as well as to the below examples unless otherwise defined.

Number average molecular weight ($M_n$), weight average molecular weight ($M_w$) and molecular weight distribution (MWD) are determined by size exclusion chromatography (SEC) using Waters Alliance GPCV 2000 instrument with online viscometer. The oven temperature is 140° C. Trichlorobenzene is used as a solvent (ISO 16014).

In detail: The number average molecular weight (Mn), the weight average molecular weight (Mw) and the molecular weight distribution (MWD) are measured by a method based on ISO 16014-1:2003 and ISO 16014-4:2003. A Waters Alliance GPCV 2000 instrument, equipped with refractive index detector and online viscosimeter was used with 3×TSK-gel columns (GMHXL-HT) from TosoHaas and 1,2,4-trichlorobenzene (TCB, stabilized with 200 mg/L 2,6-Di tert butyl-4-methyl-phenol) as solvent at 145° C. and at a constant flow rate of 1 mL/min. 216.5 μL of sample solution were injected per analysis. The column set was calibrated using relative calibration with 19 narrow MWD polystyrene (PS) standards in the range of 0.5 kg/mol to 11 500 kg/mol and a set of well characterized broad polypropylene standards. All samples were prepared by dissolving 5-10 mg of polymer in 10 mL (at 160° C.) of stabilized TCB (same as mobile phase) and keeping for 3 hours with continuous shaking prior sampling in into the GPC instrument.

Melt Strength and Melt Extensibility by Rheotens Measurement:

The strain hardening behaviour of polymers is analyzed by Rheotens apparatus (product of Göttfert, Siemensstr. 2, 74711 Buchen, Germany) in which a melt strand is elongated by drawing down with a defined acceleration. The haul-off force F in dependence of draw-down velocity v is recorded.

The test procedure is performed in a standard climatised room with controlled room temperature of T=23° C. The Rheotens apparatus is combined with an extruder/melt pump for continuous feeding of the melt strand. The extrusion temperature is 200° C.; a capillary die with a diameter of 2 mm and a length of 6 mm is used and the acceleration of the melt strand drawn down is 120 mm/s². The maximum points ($F_{max}$; $V_{max}$) at failure of the strand are characteristic for the strength and the drawability of the melt.

Intrinsic viscosity: is measured according to DIN ISO 1628/1, October 1999 (in Decalin at 135° C.).

The crosslinked fraction is assumed to be identical to the xylene hot insoluble (XHI) fraction, which is determined by extracting 1 g of finely cut polymer sample with 500 ml xylene in a Soxleth extractor for 48 hours at the boiling temperature. The remaining solid amount is dried at 90° C. and weighed for determining the insolubles amount.

Adhesion

Peel resistance (adhesive bond strength) was determined with the T-Peel Test according to ASTM D 1876-01 using an Instron 4502 tensile tester.

Test samples: extrusion coated UG kraft paper; 5 pieces, cut in machine direction, 25.4×150 mm. Samples were conditioned for one day at a relative humidity of 50±2% at 23±1° C.

The layers were separated at the desired interface, placed to the arms of the tensile tester and the force required to pull the layers apart was measured. The result was the force needed for peeling given in N/cm (peel strength in terms of load per unit width of bond line). The peeling types are defined as "fiber-tear" (if the propylene composition film being extrusion coated onto the paper substrate is separated from that paper takes fibers with it, meaning extremely good adhesion; e.g. cohesive failure in paper) or "no fibers" (no fibers are taken; pure peeling).

EXAMPLES

Materials Used

Component (A): Daploy™ WF420HMS (High melt strength polypropylene homopolymer; Borealis)
Component (B):
  (i) Priex® 25097 (Maleic anhydride grafted polypropylene random copolymer; Solvay Plastics)
  (ii) Licocene® PP MA 7452 (Maleic anhydride grafted polypropylene wax, based on metallocene technology)
  (iii) BorFlow™ HL504FB (polypropylene homopolymer with MFR of 450 g/10 min, according to ISO 1133, 230° C., 2.16 kg; Borealis)
  (iv) Sitomelt K608/1 (EVA based hot melt adhesive, Kiilto OY)
  (v) Primacor™3440 (ethylene acrylic acid copolymer, Dow) was used in a comparative example

Example 1

Preparation of Blends of Component (A) with Component (B)

The compositions were formulated by dry mixing the above described commercially available starting materials together and then melt-blended. 90 to 95 wt % of WF420HMS were mixed with 5 to 10 wt % of one of the components (B).

For the Beloit line extrusion coating, the melt-blending was carried out in a Werner&Pfleiderer ZSK40 twin-screw extruder at a temperature of 200 to 240° C. (Screw speed was 500 rpm, output was 50 kg/h).

The polymer melt strings from extruder were cooled down in a water bath and dried with air and cut into pellets.

For the Demaq line extrusion coating, the melt blending was done in a compounder BESL 10, Berstorff ZE 25 with capacity of 5-10 kg/h. It has co-rotating twin-screws, with L/D ratio 40/25. Starting materials were weighted and dry mixed together before taking them to extruder for melt blending. Set value for melt temperature was 200° C. and temperature profile was 195-200-200-200-200-200-200-200, blending was done under nitrogen flush. Set value for screw speed was 200 RPM and for feeders 7 kg/h. The polymer melt strings from extruder were cooled down in a room-temperature water bath and dried with air and cut into pellets.

Example 2-7

Extrusion coating runs were made on Beloit coextrusion coating line. Beloit line had Extruders 1&2 with size of 4,5"

and L/D 24; output was 450 kg/h (for LDPE) and Extruder 3 in size of 2,5" and L/D 30; output was 170 kg/h. It had a Peter Cloeren's die and a five layer feed block. The width of the line was 600-800 mm and the maximum line speed was 1000 m/min (design value).

In the coating line above a UG kraft paper (UPM Prime Wrap) having a basis weight of 70 g/m² was coated with a co-extruded structure, which was composed of 20 g/m² of WF420HMS on the top layer and 20 g/m² of WF420HMS respectively of blends prepared according to Example 1 in the layer against paper. Together all coatings had a basis weight of 40 g/m². The temperature of the polymer melt was set to 290° C. and the extruders' temperature profile was 200-240-290-290° C. The chill roll was matt and temperature of its surface was 15° C. Used die opening was 0.65 mm and nip distance was 160 mm. Melt film touched the substrate for the first time+10 mm from nip to substrate side. Pressure of the pressure roll was 3.0 kp/cm². The line speed was 100 m/min.

5 test samples (25.4×150 mm) of WF420HMS coated paper, as well as of WF420 HMS-blend coated paper were tested regarding adhesion by the T-Peel Test according to ASTM D 1876 on an Instron Tensile Tester.

Results are Summarized in Table 1

TABLE 1

Adhesion Test - no pre-treatments

| Example | Coating Material Component (A)/(B) [wt %] | Load [N] | s.d. | Load/width [N/cm] | s.d. | Improvement [%] |
|---|---|---|---|---|---|---|
| 2 | WF420HMS[100] | 0.73 | 0.04 | 0.29 | 0.016 | 0 |
| 3 | WF420HMS[90]/ Priex 25097[10] | 1.56 | 0.118 | 0.61 | 0.046 | 113 |
| 4 | WF420HMS[95]/ Licocene PP MA 7452 [5] | 1.71 | 0.077 | 0.67 | 0.030 | 134 |
| 5 | WF420HMS[90]/ BorFlow HL504FB [10] | 0.91 | 0.083 | 0.36 | 0.033 | 24 |
| 6 | WF420HMS[90]/ Sitomelt K608/1 [10] | 1.05 | 0.048 | 0.41 | 0.019 | 43 |
| 7 | WF420HMS[90]/ Primacor 3440 [10] | 0.47 | 0.048 | 0.19 | 0.019 | −35 |

Example 7 is a Comparative Example s.d. Standard deviation
All samples showed pure peeling, "no fiber" peeling type
Improvement in % is compared to the adhesion value of Example 2 (pure WF420HMS).

Example 8-13

Extrusion coating runs were made on Beloit coextrusion coating line as described for Examples 2-7.

In the coating line above a UG kraft paper (UPM Prime Wrap) having a basis weight of 70 g/m² was coated with a co-extruded structure, which was composed of 20 g/m² of WF420HMS on the top layer and 20 g/m² of WF420HMS respectively of blends, prepared according to Example 1, in the layer against paper. Together all coatings had a basis weight of 40 g/m². The temperature of the polymer melt was set to 290° C. and the extruders' temperature profile was 200-240-290-290° C. The chill roll was matt and temperature of its surface was 15° C. Used die opening was 0.65 mm and nip distance 160 mm. Melt film touched the substrate for the first time+10 mm from nip to substrate side. Pressure of the pressure roll was 3.0 kp/cm². The line speed was 100 m/min.

Ozone treatment for the melt (Sherman) and Corona treatment for the substrate (Vetaphone) have been employed for all samples. Sherman ozone treater had a maximum output power of 4.0 kW and ozone concentration around 30 g/m³. Set point for ozone was 2.6 kW and thus concentration of ozone was 19-20 g/m³. Applicator's distance and angle from molten film was 70 mm and 45°. Veta phone ET5 corona treater had a output power of 12 kW and frequency of 18 to 35 kHz. It had an HF-amplifier with output voltage of 15 to 25 kV and multi-profile aluminium electrode. Set point for used corona was 12.0 kW.

5 test samples (25.4×150 mm) of WF420HMS coated paper, as well as of WF420 HMS-blend coated paper were tested regarding adhesion by the T-Peel Test according to ASTM D 1876 on an Instron Tensile Tester.

Results are Summarized in Table 2:

TABLE 2

Adhesion: Test- ozone and corona pre-treatment.

| Example | Coating Material Component (A)/(B) [wt %] | Load [N] | s.d. | Load/width [N/cm] | s.d. | Improvement [%] |
|---|---|---|---|---|---|---|
| 8 | WF420HMS[100] | 2.10 | 0.109 | 0.83 | 0.043 | 0 |
| 9 | WF420HMS[90]/ Priex 25097[10] | 2.33 | 0.106 | 0.92 | 0.042 | 10 |

TABLE 2-continued

Adhesion: Test- ozone and corona pre-treatment.

| Example | Coating Material Component (A)/(B) [wt %] | Load [N] | s.d. | Load/width [N/cm] | s.d. | Improvement [%] |
|---|---|---|---|---|---|---|
| 10 | WF420HMS[95]/ Licocene PP MA 7452 [5] | 3.51 | 0.438 | 1.38 | 0.173 | 66 |
| 11 | WF420HMS[90]/ BorFlow HL504FB [10] | 2.11 | 0.181 | 0.83 | 0.071 | 0 |
| 12 | WF420HMS[90]/ Sitomelt K608/1 [10] | 3.64 | 0.803 | 1.43 | 0.316 | 72 |
| 13 | WF420HMS[90]/ Primacor 3440 [10] | 1.99 | 0.093 | 0.78 | 0.037 | −6 |

Example 13 is a Comparative Example s.d. standard deviation

Samples 8-11 and sample 13 showed "fiber-tear" peeling type, e.g. cohesive failure in the paper For Sample 12 the failure was "fiber-tear" for 2 of 5 pieces and "no fiber" for 3 of 5 pieces.

Improvement in % is compared to the adhesion value of Example 8 (pure WF420HMS).

Example 14-19

Extrusion coating runs were made on a Demag coating line. It was a cast film line adapted to extrusion coating. The nip configuration differed from conventional extrusion coating line's horizontal die placing by the die being in 45° angle from horizontal direction; however the molten film was coming to the nip tangential to chill roll as normally. Demaq line had an extruder with L/D ratio 45/31 and maximum output was 60 kg/h. There were no back pressure valves in Demaq. The die was a Ultraflex R75 450 mm (Extrusion Dies Inc.). The maximum width of the paper roll for the line was 420 mm and the maximum line speed was 200 m/min (design value). Chill roll was glossy and maximum pressure for pressure roll was 6 bar.

In the coating line above a UG kraft paper (UPM Prime Wrap) having a basis weight of 70 g/m² was coated in monolayer structures with a layer of WF420HMS, respectively of blends, prepared according to Example 1, all having a basis weight of 40 g/m². The temperature of the polymer melt was set to 290° C. The line speed was 20 m/min. Die opening was 0.5 mm, nip distance 170 mm and nip pressure 6 bar.

5 test samples (25.4×150 mm) of WF420HMS coated paper, as well as of WF420HMS-blend coated paper were tested regarding adhesion by the T-Peel Test according to ASTM D 1876 on an Instron Tensile Tester.

Results are Summarized in Table 3:

TABLE 3

Adhesion Test - no pre-treatments

| Example | Coating Material Component (A)/(B) [wt %] | Load [N] | s.d. | Load/width [N/cm] | s.d. | Improvement [%] |
|---|---|---|---|---|---|---|
| 14 | WF420HMS[100] | 1.426 | 0.216 | 0.56 | 0.085 | 0 |
| 15 | WF420HMS[90]/ Priex 25097[10] | 1.916 | 0.145 | 0.75 | 0.057 | 34 |
| 16 | WF420HMS[90]/ Licocene PP MA 7452 [10] | 4.986 | 0.235 | 1.956 | 0.093 | 249 |
| 17 | WF420HMS[90]/ BorFlow HL504FB [10] | 1.901 | 0.217 | 0.75 | 0.086 | 33 |
| 18 | WF420HMS[90]/ Sitomelt K608/1 [10] | 1.927 | 0.123 | 0.76 | 0.049 | 35 |
| 19 | WF420HMS[90]/ Primacor 3440 [10] | 1.132 | 0.198 | 0.45 | 0.078 | −21 |

Example 19 is a Comparative Example s.d. standard deviation

Improvement in % is compared to the adhesion value of Example 14 (pure WF420HMS).

What is claimed is:

1. An extrusion coated article comprising a paper substrate and at least one layer of a two-component adhesion composition suitable for extrusion coating paper substrates on at least one surface of the article, the two-component adhesion composition comprising:
   a) from 70 to 98 wt % of high melt strength polypropylene (A) with a branching index g' of 0.9 or less, wherein the cross-linked fraction of the polypropylene (A) does not exceed 1.0 wt %, determined as the relative amount of polymer insoluble in boiling xylene (xylene hot insoluble fraction, XHI); and
   b) from 2 to 30 wt % of a component (B) selected from the group consisting of:
      (i) maleic anhydride-modified polypropylene (MAPP); or
      (ii) maleic anhydride-modified polypropylene wax;

wherein the high melt strength polypropylene (A) has been obtained by treating an unmodified polypropylene (A') with a peroxide and with a bifunctional monomer selected from the group consisting of butadiene, isoprene, dimethyl butadiene and divinyl benzene.

2. The extrusion coated article according to claim 1, wherein the high melt strength polypropylene (A) is a propylene homopolymer.

3. The extrusion coated article according to claim 1, wherein the maleic anhydride-modified polypropylene (i) is a random copolymer of propylene and ethylene.

4. The extrusion coated article according to claim 1, wherein the maleic anhydride-modified polypropylene (i) has a content of maleic anhydride in the modified polypropylene in the range of 0.001 to 10 wt %, based on the weight of the modified polypropylene.

5. The extrusion coated article according to claim 1, wherein the maleic anhydride-modified polypropylene wax (ii) has been obtained by grafting an unmodified polypropylene wax, which was prepared in the presence of a metallocene catalyst.

6. The extrusion coated article according to claim 1, wherein the maleic anhydride-modified polypropylene wax (ii) has been obtained by grafting an unmodified polypropylene wax, which had a weight average molecular weight of the polypropylene waxes of less than 10,000 g/mol.

7. The extrusion coated article according to claim 1, wherein the maleic anhydride-modified polypropylene wax (ii) has a content of maleic anhydride in the modified polypropylene was in the range of 0.1 to 20 wt % based on the weight of the modified polypropylene.

8. The article according to claim 1, which is a packaging material.

* * * * *